United States Patent [19]

Kajihara et al.

[11] 4,232,007

[45] Nov. 4, 1980

[54] ORAL ANTILIPEMIC AGENTS

[75] Inventors: Motoyoshi Kajihara; Toshihiro Hamakawa, both of Naruto; Toshiaki Shibata, Tokushima; Takashi Suzue, Naruto; Setsuro Fujii, Tokushima, all of Japan

[73] Assignee: Taiho Pharmaceutical Company Ltd., Tokyo, Japan

[21] Appl. No.: 704,933

[22] Filed: Jul. 12, 1976

[30] Foreign Application Priority Data

Aug. 26, 1975 [GB] United Kingdom ............... 35250/75

[51] Int. Cl.³ .............................................. A61K 37/00
[52] U.S. Cl. .................................................... 424/177
[58] Field of Search ................................. 424/78, 177

[56] References Cited

U.S. PATENT DOCUMENTS

| 3,503,951 | 3/1970 | Iselin | 424/177 |
| 3,669,689 | 6/1972 | Hoshino | 424/177 |
| 3,849,554 | 11/1974 | Winitz | 424/177 |

Primary Examiner—Frederick E. Waddell
Attorney, Agent, or Firm—Toren, McGeady and Stanger

[57] ABSTRACT

An oral antilipemic agent comprising a pharmaceutically effective amount of at least one of acidic polyamino acids having a molecular weight of 10,000 to 100,000 and pharmaceutically acceptable salts thereof, and an adjuvant.

1 Claim, No Drawings

ORAL ANTILIPEMIC AGENTS

BACKGROUND OF THE INVENTION

This invention relates to oral antilipemic agents for remarkably reducing lipids in blood, especially total lipid, cholesterol, triglycerides and β-lipoprotein, etc.

Despite the intensive research heretofore carried out for more than one century, the causes of arteriosclerosis have not been fully clarified yet and various mechanisms for its occurrence have been explained merely with hypotheses. In recent years, however, it is considered to be attributable to lipids' metabolism disorders, cholesterol and triglycerides which have been implicated as especially important factors. Among various drugs provided for controlling these factors, heparin, dextran sulfate and similar acidic substances are known to be effective in reducing lipids in blood, but heparin and dextran sulfate have drawbacks. They possess a very high anticoagulant activity as a side effect and cannot be administered continually for a long period of time.

SUMMARY OF THE INVENTION

An object of this invention is to provide antilipemic agents which can be orally administered and are free of the above-mentioned drawbacks of the known drugs.

Another object of this invention is to provide oral antilipemic agents which act very effectively in reducing lipids in blood.

Another object of this invention is to provide oral antilipemic agents which are free of side effects and can be administered continually for a long period of time.

Another object of this invention is to provide oral antilipemic agents having no toxicity.

This invention provides an antilipemic agent containing as an effective component at least one member from the group of acidic polyamino acids having a molecular weight of 10,000 to 100,000 and pharmaceutically acceptable salts thereof.

Conventionally, polyamino acids have found only limited applications for medical treatment as microcapsules, artificial skins, surgical threads, etc. in which the only physical properties of the acids are utilized but no use whatever was made of its pharmacological activity. Focusing our attention on the heretofore unknown pharmacological activity of polyamino acids, especially of acidic polyamino acids, we have succeeded in developing novel antilipemic agents.

Unlike polysaccharides, such as, for example, heparin, and dexran sulfate, the acidic polyamino acids and pharmaceutically acceptable salts thereof of this invention act very effectively to reduce the lipids in blood. Further, the compounds of the invention exhibit a very low anticoagulant activity (about 1/5,000 of heparin) which activity is the most objectionable side effect of polysaccharides. Accordingly the compounds of the invention can be administered continually for a long period of time. Because of oral administration, the compounds of the invention will not be deposited in the liver and kidney and are therefore free of side effects, such as, denaturation and necrosis which would otherwise be unavoidable. Thus the compounds of the invention are usable as excellent antilipemic agents.

In this invention, the acidic polyamino acids and the pharmaceutically acceptable salts thereof are included within the scope of the invention.

DESCRIPTION OF THE PREFERRED EMBODIMENT

The acidic polyamino acids of this invention are known compounds and are homopolymers of acidic amino acids, copolymers of acidic amino acids, and copolymers of acidic amino acids and amino acids other than acidic amino acids which copolymers are composed predominantly of acidic amino acids. Examples of homopolymers of acidic amino acids are polyaspartic acid, polyglutamic acid, polycysteic acid, etc. Copolymers of acidic amino acids are those prepared by copolymerizing at least two acidic amino acids such as, for example, a copolymer of aspartic acid and glutamic acid, a copolymer of glutamic acid and cysteic acid, a copolymer of cysteic acid and aspartic acid, and a copolymer of aspartic acid, glutamic acid and cysteic acid. Examples of amino acids other than acidic amino acids to be copolymerized with acidic amino acids to prepare copolymers mainly composed of acidic amino acids are glycine, alanine, phenylalanine, valine, leucine, isoleucine and similar neutral amino acids; serine, threonine, tyrosine and similar hydroxyamino acids; and lysine, arginine and like basic amino acids. Among these acidic polyamino acids, preferable homopolymers and copolymers are of acidic amino acids, and more preferable are polyaspartic acid, polyglutamic acid, polycysteic acid and copolymers of at least two of aspartic acid, glutamic acid and cysteic acid.

Exemplary of pharmaceutically acceptable salts of acidic polyamino acids are alkali metal salts and alkaline earth metal salts of acidic polyamino acids. Examples of alkali metal salts thereof are lithium salts, sodium salts, potassium salts of acidic polyamino acids, among which sodium salts and potassium salts are preferable. Alkaline earth metal salts of acidic polyamino acids include, for example, magnesium, calcium, strontium and barium salts, among which magnesium salts and calcium salts are preferable.

The molecular weights of the compounds of this invention are usually 10,000 to 100,000, preferably 30,000 to 90,000. With the molecular weight outside the range of 10,000 to 100,000, the acidic polyamino acids and pharmaceutically acceptable salts thereof are insufficient in reducing the lipids in blood, hence undesirable. The molecular weight can be adjusted for example with a molecular sieve, such as, Sephadex (trade mark, product of Pharmacia Fine Chemical, Sweden), Dia Filter (trade mark, product of Nihon Shinku Gijutsu Co., Ltd., Japan) or the like.

The compounds of this invention can be prepared by the usual processes for the synthesis of polyamino acids and salts thereof, for example, as disclosed by E. R. Blout in J. Am. Chem. Soc. 78, 941 (1956). More specifically stated, the sodium salt of polyglutamic acid, for example, can be prepared by the following process. L-glutamic acid is first suspended in methanol, and hydrogen chloride gas is passed through the suspension to obtain the methyl ester of the acid. The ester is then suspended in dioxane, and phosgene gas is introduced into the suspension to prepare N-carboxylic anhydride, which is thereafter dissolved in ethylene dichloride. Triethylamine serving as a polymerization initiator is added to the solution to effect polymerization. The resulting reaction mixture is saponified with a dilute aqueous solution of sodium hydroxide for demethylation, whereby the sodium salt of polyglutamic acid is obtained. The above reactions are represented by the following equations:

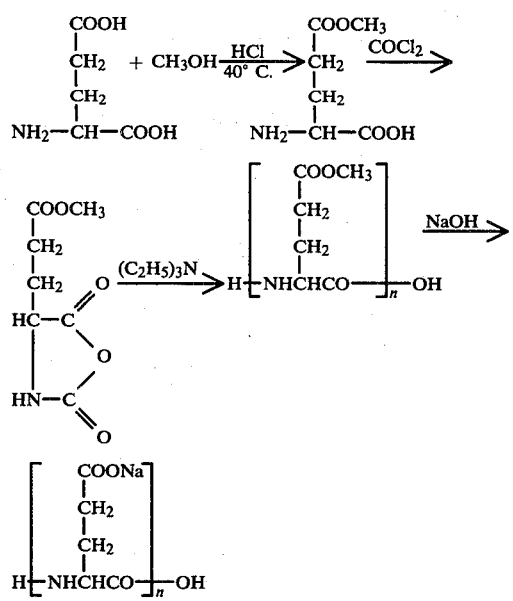

Given below is another specific example of the processes. Sulfuric acid and benzyl alcohol are added for example to L-aspartic acid, and the resulting reaction mixture is neutralized to precipitate γ-benzyl-L-aspartic acid. The acid is suspended in dioxane, and phosgene gas is introduced into the suspension to obtain N-carboxylic anhydride, which is dissolved in dioxane again. Triethylamine as a polymerization initiator is added to the solution to effect polymerization. The reaction mixture is added to the alcohol to obtain a precipitate, the precipitate is dissolved in glacial acetic acid, and hydrogen bromide gas is passed through the solution for debenzylation to give polyaspartic acid.

Alkali salts of acidic polyamino acids of this invention can also be prepared from commercially avialable methyl esters of acidic polyamino acids, such as, Ajicoat A-2000, XB-900, XB-400, TC-10 and S-30 manufactured by Ajinomoto Co., Inc., Japan, PLG-10 and PLG-20 manufactured by Kyowa Hakko Kogyo Co., Ltd., Japan, etc. by demethylating these esters in known manner. Demethylation can be effected for example by saponifying an ester of acidic polyamino acid with the addition of a mixture of aqueous alkali solution and alcohol, ether, chloroform or the like. Acidic polyamino acids in the form of free acid can be prepared, for example, by treating the above alkali salts of polyamino acids with acid, such as, hydrochloric acid.

The antilipemic agent of this invention can be orally administered in the form of a pharmaceutical composition comprising as an effective ingredient at least one compound of this invention in association with a pharmaceutical vehicle, excipient or similar adjuvant. The composition can be in the form of, for example, a coated or uncoated tablet, hard or soft gelatin capsule, or suspension. Methods other than oral administration permit deposition of acidic polyamino acids in the liver and kidney and are not desirable therefore.

Examples of suitable vehicles or excipients are talc, magnesium stearate, milk sugar, saccharose, cyrstalline cellulose, methyl cellulose, carboxymethyl cellulose, glycerine, sodium alginate, gum arabic, starches, kaolin, etc.

When in dosage unit form, the composition may contain from 100 to 500 mg of active ingredient per dosage unit.

The antilipemic agent of this invention is orally administered usually in a dose of about 500 to 1,000 mg/day calculated as the active ingredient.

Examples of this invention are given below.

EXAMPLE 1

A 100 g quantity of the methyl ester of polyglutamic acid (average molecular weight: 100,000) is dissolved in dichloroethane to a concentration of 10 wt.%. To the solution is added a mixture of 70 ml of 2 N sodium hydroxide solution, 140 ml of methanol and 140 ml of isopropanol, and the resulting mixture is stirred at room temperature for about 8 hours to effect demethylation. The product is then passed through a molecular sieve (Sephadex G-200) for the classification of molecular weight to separate a portion ranging from 80,000 to 100,000 in molecular weight (average molecular weight: 90,000). The separated portion is concentrated under reduced pressure and divided into two portions of equivalent weight. To one of the portions is added methanol and the precipitate formed is separated by filtration and dried to obtain the sodium salt of polyglutamic acid. To the other portion is added concentrated hydrochloric acid until the pH thereof reaches 4, then the solution is cooled with ice, whereby a precipitate is formed. The precipitate is separated by filtration, washed with diluted hydrochloric acid, thereafter with methanol and dried to obtain polyglutamic acid. Each powder (200 mg) of polyglutamic acid and sodium salt thereof thus obtained is mixed with 290 mg of milk sugar, 500 mg of corn starch and 10 mg of hydroxypropyl cellulose and the mixtures obtained are granulated respectively. The granules are suspended in water. Two kinds of the suspensions are orally administered to 7 rats in a dose of 50 mg/kg, respectively, to determine the reduction of lipids in blood. The rat used for test has been intravenously given a surfactant, Triton WR-1339 (trade mark, product of Ruger Chemical Corp., U.S.A.) in an amount of 200 mg/kg, previously to increase the lipids in blood. The test results are listed in Table 1.

Table 1

| | Normal rat | Rat given surfactant | Rat administered with: | |
|---|---|---|---|---|
| | | | Sodium salt of polyglutamic acid | Polyglutamic acid |
| Total lipid | 220 ± 12 | 1033 ± 330 | 393 ± 66 | 373 ± 132 |
| Triglyceride | 44.7 ± 3.5 | 780.1 ± 354.5 | 92.0 ± 42.8 | 103.3 ± 67.2 |
| Total cholesterol | 89.9 ± 10.4 | 235.3 ± 41.7 | 121.8 ± 18.9 | 118.1 ± 35.3 |
| Free cholesterol | 25.7 ± 3.7 | 114.2 ± 28.8 | 40.0 ± 11.4 | 38.8 ± 11.7 |
| β-Lipoprotein | 44.3 ± 1.3 | 141.7 ± 28.8 | 63.4 ± 16.9 | 61.9 ± 29.0 |

Note: (Unit: mg/dl of plasma).

EXAMPLE 2

Methyl ester of polyaspartic acid (average molecular weight: 35,000) is demethylated in the same manner as in Example 1, and the product is passed through a molecular sieve (Dia Filter) for the classification of molecular weight to separate a portion ranging from 10,000 to 50,000 in molecular weight (average molecular weight: 30,000). The separated portion is concentrated under reduced pressure, methanol is added to the concentrate and the resulting precipitate is separated by filtration and dried to obtain the sodium salt of polyaspartic acid. With the powder (100 mg) thus obtained are mixed 76 mg of milk sugar, 108 mg of corn starch, 58 mg of crystalline cellulose and 8 mg of talc. The mixture is encapsulated. The capsules are orally administered in a dose of 50 mg/kg to 5 dogs which have been orally given olive oil (each in 10 ml/kg) previously to increase the lipids in blood. Similar test results to those obtained in Example 1 are observed.

EXAMPLE 3

The methyl ester of polycysteic acid (average molecular weight: 65,000) is demethylated in the same manner as in Example 1, and the product is passed through a molecular sieve (Sephadex G-100) for the classification of molecular weight to separate a portion ranging from 40,000 to 80,000 in molecular weight (average molecular weight: 60,000). The separated portion is concentrated under reduced pressure and treated with conc. HCl solution to form a precipitate. The precipitate is filtered off, washed with dil. HCl solution, then with methanol and dried to obtain polycysteic acid. With the powder (200 mg) thus obtained are mixed 290 mg of milk sugar, 500 mg of corn starch and 10 mg of hydroxypropyl cellulose. The mixture is granulated. The granules are orally administered in a dose of 50 mg/kg to 5 rabbits which have been orally given olive oil in an amount of 10 ml/kg respectively, previously to increase the lipids in blood. The similar test results as in Example 1 are observed.

EXAMPLE 4

The methyl ester of a copolymer of glutamic acid and aspartic acid (1:1) (average molecular weight: 35,000) is demethylated in the same manner as in Example 1, and the product is passed through a molecular sieve (Dia Filter) for the classification of molecular weight to separate a portion ranging from 10,000 to 50,000 in molecular weight (average molecular weight: 30,000). The separated portion is concentrated under reduced pressure, methanol is added to the concentrate and the resulting precipitate is filtered off and dried to obtain the sodium salt of the copolymer of glutamic acid and aspartic acid. With the powder (200 mg) thus obtained are mixed 290 mg of milk sugar, 500 mg of corn starch and 10 mg of hydroxypropyl cellulose. The mixture is granulated and the granules are suspended in an isotonic sodium chloride solution. The suspension is orally administered in a dose of 50 mg/kg to 7 rats which have been intravenously given a surfactant, Triton WR-1339 in an amount of 200 mg/kg respectively, previously to increase the lipids in blood. The similar test results as in Example 1 are observed.

EXAMPLE 5

The powder (100 mg) of polyglutamic acid (average molecular weight: 90,000) prepared in the same manner as in Example 1, 33 mg of milk sugar, 14 mg of corn starch and 3 mg of talc are mixed together, granulated and compressed to a tablet. The tablet is coated with 10 mg of hydroxypropyl methyl cellulose to prepare a finished tablet. One dose (50 mg/kg) of the tablets is orally administered to 5 dogs which have been orally given olive oil in an amount of 10 ml/kg respectively, previously to increase the lipids in blood. The similar test results as in Example 1 are observed.

Antilipemic agents of this invention are tested for biochemical activities. The results are given below. 1. Acute toxicity test The polyglutamic acid obtained in Example 1 and heparin are orally administered to the animals indicated in Table 3 below to determine the $LD_{50}$ values 72 hours after the administration. The results are given in Table 2.

Table 2

| Compound tested | Animal | Method of administration | $LD_{50}$ |
|---|---|---|---|
| Polyglutamic acid | Rat | Intravenous | 2.05 g/kg |
| Polyglutamic acid | " | Oral | 6 g/kg |
| Heparin | " | Intravenous | 0.73 g/kg |
| " | " | Oral | 1.95 g/kg |

The table reveals that the polyglutamic acid has much lower toxicity than heparin. 2. Recalcification test A 0.5 ml quantity of 0.1 M sodium citrate is added to 4.5 ml of blood of rat to obtain plasma. To 0.2 ml portions of the plasma are added the polyglutamic acid of Example 1, heparin and dextran sulfate respectively, in the amounts listed in Table 4 below. Thereafter 0.1 ml of 0.025 M $CaCl_2$ saline solution is added to coagulate the blood sample. The time taken for coagulation is determined with the results given in Table 3.

Table 3

| Amount ($\mu$g) | Coagulation time (sec.) | | |
|---|---|---|---|
| | Polyglutamic acid | Heparin | Dextran sulfate |
| 0 | 58 | 58 | 58 |
| 0.1 | 55 | 62 | 57 |
| 0.3 | 58 | 145 | 62 |
| 0.5 | 56 | 168 | 61 |
| 1 | 62 | 285 | 117 |
| 10 | 58 | No coagulation | 172 |
| 100 | 62 | " | No coagulation |
| 500 | 100 | " | " |
| 1000 | 151 | " | " |
| 2000 | 250 | " | " |

What we claim is:

1. A therapeutic method for reducing lipids in blood which comprises administering an antilipemically effective amount of the oral antilipemic agent comprising a pharmaceutically effective amount of at least one acidic polyamino acid having a molecular weight of 10,000 to 100,000 and pharmaceutically acceptable salts thereof, and an adjuvant to a patient affected with hyperlipidemia.

* * * * *